US006936402B2

(12) United States Patent
Kim et al.

(10) Patent No.: US 6,936,402 B2
(45) Date of Patent: Aug. 30, 2005

(54) MONOMERS CONTAINING AN OXEPAN-2-ONE GROUP, PHOTORESIST COMPOSITIONS COMPRISING POLYMERS PREPARED FROM THE MONOMERS, METHODS FOR PREPARING THE COMPOSITIONS, AND METHODS FOR FORMING PHOTORESIST PATTERNS USING THE COMPOSITIONS

(75) Inventors: Jin-Baek Kim, Seoul (KR); Tae-Hwan Oh, Gangwon-do (KR); Jae-Hak Choi, Daejeon (KR); Jae-Jun Lee, Kyunggi-do (KR)

(73) Assignee: Korea Advanced Institute Science & Technology, Daejeon (KR)

( * ) Notice: Subject to any disclaimer, the term of this patent is extended or adjusted under 35 U.S.C. 154(b) by 0 days.

(21) Appl. No.: 10/784,806

(22) Filed: Feb. 24, 2004

(65) Prior Publication Data
US 2005/0042539 A1 Feb. 24, 2005

(30) Foreign Application Priority Data
Aug. 23, 2003 (KR) .................... 10-2003-0058525

(51) Int. Cl.$^7$ ............. G03C 1/73; G03F 7/039; G03F 7/20; G03F 7/30; C07D 313/06; C08F 24/00

(52) U.S. Cl. ............. 430/270.1; 430/905; 430/910; 430/914; 430/325; 430/326; 430/330; 430/311; 430/945; 430/942; 430/966; 549/268; 549/271; 549/272; 526/266; 526/280; 526/281; 526/284; 526/271

(58) Field of Search ............... 549/268, 271, 549/272; 526/266, 280, 284, 271, 281; 430/270.1, 905, 910, 966, 945, 942, 325, 326, 330, 311, 319, 914

(56) References Cited

U.S. PATENT DOCUMENTS

| 4,491,628 A | 1/1985 | Ito et al. ............. 430/176 |
| 4,732,838 A | * 3/1988 | Sechi et al. ............ 430/198 |
| 5,763,366 A | * 6/1998 | Takatsuto et al. ......... 504/291 |
| 5,968,713 A | 10/1999 | Nozaki et al. ............ 430/326 |
| 6,090,952 A | * 7/2000 | Hazra et al. ............. 549/268 |
| 6,667,243 B1 | * 12/2003 | Ramsbey et al. ......... 438/710 |

OTHER PUBLICATIONS

Kim et al "Nonshrinkable Photoresists for ArF Lithography", Advances in Resist Technology and Processing XX, Proceedings o SPIE vol.5039 (2003), p. 689–697.*

Chang, F. C., "Potential Bile Acid Metabolites. 2. 3,7, 12–Trisubstituted 5β–Cholanic Acids," *J. Org. Chem.* 44:4567–4572, American Chemical Society (1979).

Hien, S., et al., "Photoresist Outgassing at 157 nm Exposure," *Proc. SPIE* 4345:439–447, SPIE (2001).

* cited by examiner

Primary Examiner—Sin J. Lee
(74) Attorney, Agent, or Firm—Sterne, Kessler, Goldstein & Fox P.L.L.C.

(57) ABSTRACT

Disclosed herein is a novel norbornene, acrylate or methacrylate monomer as a photoresist monomer containing an oxepan-2-one group. Further disclosed are photoresist compositions comprising a polymer prepared from the monomer, methods for preparing the photoresist compositions, and methods for forming photoresist patterns using the photoresist compositions.

29 Claims, 1 Drawing Sheet

300 nm 280 nm 260 nm 240 nm

220nm

200nm

MONOMERS CONTAINING AN OXEPAN-2-ONE GROUP, PHOTORESIST COMPOSITIONS COMPRISING POLYMERS PREPARED FROM THE MONOMERS, METHODS FOR PREPARING THE COMPOSITIONS, AND METHODS FOR FORMING PHOTORESIST PATTERNS USING THE COMPOSITIONS

BACKGROUND OF THE INVENTION

This application claims priority to Korean Patent Application 10-2003-58525, filed Aug. 23, 2003, which is incorporated by reference herein in its entirety.

1. Field of the Invention

The present invention relates to a norbornene monomer, an acrylate monomer and a methacrylate monomer containing an oxepan-2-one group, and methods for preparing the monomers. In some embodiments, the present invention relates to a norbornene monomer, an acrylate monomer and a methacrylate monomer containing a novel oxepan-2-one group which can be used to prepare photoresist compositions, and methods for preparing the monomers.

The present invention also relates to photoresist compositions and methods for preparing the photoresist compositions. The present invention relates to a photoresist composition comprising a polymer prepared by homopolymerizing a monomer selected from norbornene, acrylate and methacrylate monomers, or copolymerizing the monomer with another monomer. The photoresist composition makes it possible to form high-resolution patterns even in the far ultraviolet region:

The present invention also relates to methods for forming patterns using the photoresist compositions.

2. Description of the Related Art

In recent years, in order to attain high sensitivity in fine fabrication technology for production of semiconductor devices, special attention has been paid to chemically amplified photoresists suitable for lithography using a light source in the far ultraviolet region, such as a KrF excimer laser (248 nm), an ArF excimer laser (193 nm) or an $F_2$ excimer laser (157 nm). These photoresists are typically fabricated by blending a photoacid generator, an acid labile photoresist polymer, a dissolution inhibitor, etc.

In general, upon exposure of the chemically amplified photoresists to light, a large variation in the polarity of the dissolution inhibitor bonded to the polymer backbone is caused by the catalytic action of an acid generated from the photoacid generator. The development of the photoresist with a polar or non-polar solvent leads to the formation of positive- or negative-type photosensitive patterns.

Copolymers consisting of norbornene and maleic anhydride (COMA), methacrylate copolymers developed by Fujitsu Ltd., Japan (U.S. Pat. No. 5,968,713), copolymers consisting of vinylether and maleic anhydride (VEMA) developed by Samsung Electronics, Korea, and ROMA-type copolymers developed by Kumho, Korea, are examples of representative chemically amplified photoresist polymers for an ArF excimer laser.

These copolymers use esters of tert-butyl, acetals of ethoxyethyl, ketals, etc., as carboxylprotecting groups. However, these protecting groups release low molecular weight organic substances such as isobutene, ethyl vinyl ether, acetaldehyde and ethanol as byproducts due to photogenerated acids upon exposure and post-exposure bake.

The released low molecular weight organic substances are readily volatile, causing a change in the volume of the photoresist film and forming an organic film on the lens surface of an exposure device. The organic film formation lowers the transmittance of the lens and thus results in low productivity of the photoresist and pattern deformation (Hien, S., et al., Francis M. Houlihan, Ed., Proceedings of SPIE, Vol. 4345, p 439, 26th International Symposium on Microlithography, Santa Clara, Calif. (2001)).

Thus, there is a need for novel chemically amplified photoresists without volatilization of any chemical substances from photoresist polymers in the course of lithographic processes.

SUMMARY OF THE INVENTION

The present invention relates to synthesized photoresist polymers having an alicyclic structure which exhibit a high light transmittance in the far UV region such as from an ArF excimer laser (193 nm), excellent etch resistance and thermal stability. Since the photoresist polymers of the present invention do not release low molecular weight organic substances during the lithographic process, they do not contaminate the lens of an exposure device and thus do not cause decreased productivity and pattern deformation.

A first embodiment of the present invention is directed to a norbornene monomer, an acrylate monomer and a methacrylate monomer containing a novel oxepan-2-one group which can be used to prepare photoresist polymers capable of forming high-resolution patterns even in the far ultraviolet region.

A second embodiment of the present invention is directed to a method for preparing the norbornene, acrylate and methacrylate monomers containing an oxepan-2-one group.

A third embodiment of the present invention is directed to a photoresist composition prepared using the norbornene, acrylate and methacrylate monomers.

A fourth embodiment of the present invention is directed to a method for preparing a photoresist composition.

A fifth embodiment of the present invention is directed to a method for forming photoresist patterns using a photoresist composition.

DETAILED DESCRIPTION

Figure 1:
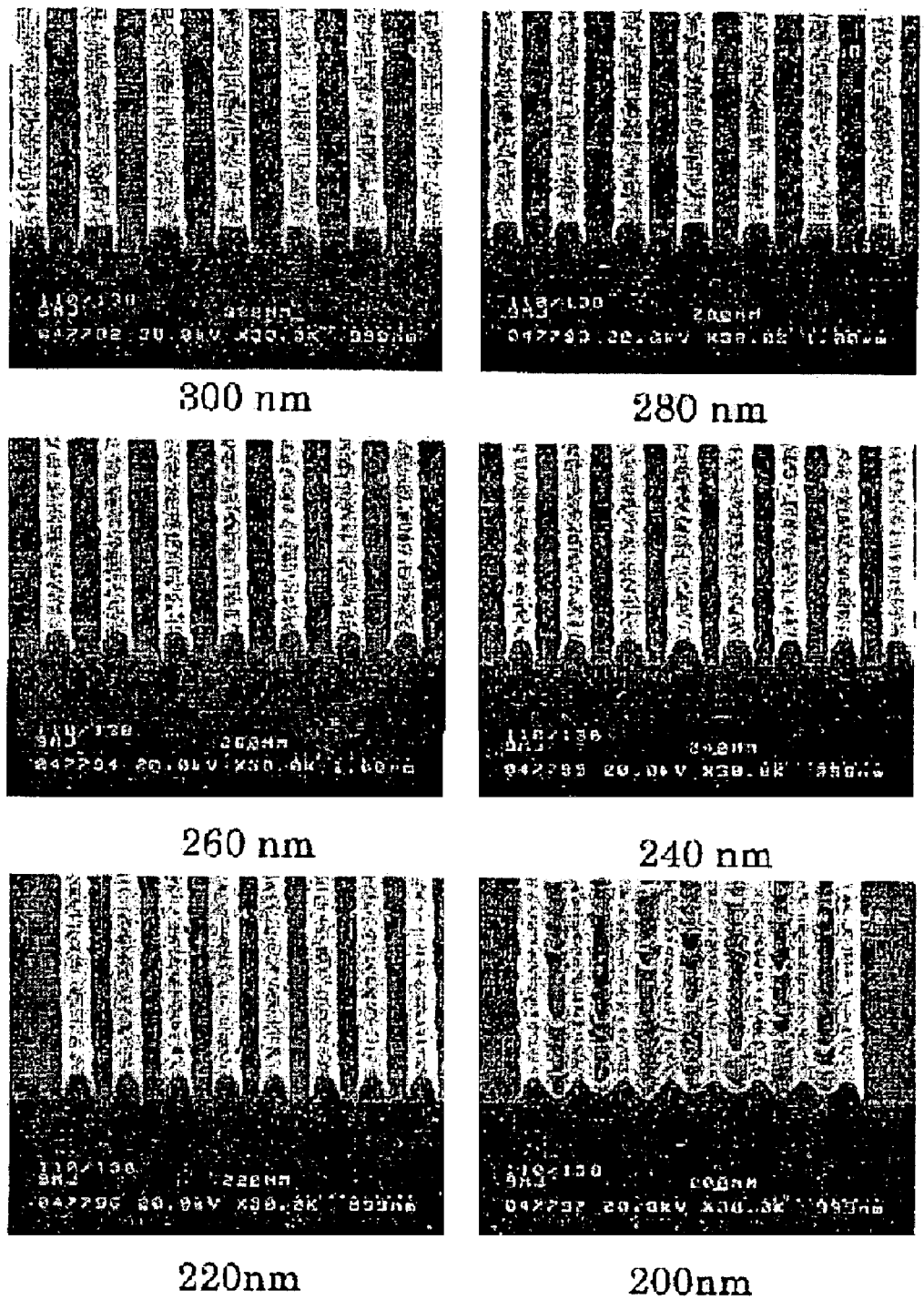
FIG. 1 is an electron microscope image showing photoresist patterns formed as described in Example 19.

The present invention relates to synthesized photoresist polymers having an alicyclic structure which exhibit a high light transmittance in the far UV region such as from an ArF excimer laser (193 nm), excellent etch resistance and thermal stability. Since the photoresist polymers of the present invention do not release low molecular weight organic substances during the lithographic process, they do not contaminate the lens of an exposure device and thus do not cause decreased productivity and pattern deformation.

A first embodiment of the present invention is directed to a norbornene monomer, an acrylate monomer and a methacrylate monomer containing a novel oxepan-2-one group which can be used to prepare photoresist polymers capable of forming high-resolution patterns even in the far ultraviolet region.

A second embodiment of the present invention is directed to a method for preparing the norbornene, acrylate and methacrylate monomers containing an oxepan-2-one group.

A third embodiment of the present invention is directed to a photoresist composition prepared using the norbornene, acrylate and methacrylate monomers.

A fourth embodiment of the present invention is directed to a method for preparing a photoresist composition.

A fifth embodiment of the present invention is directed to a method for forming photoresist patterns using a photoresist composition.

In the first embodiment of the present invention, norbornene, acrylate and methacrylate monomers containing an oxepan-2-one group, are represented by one of Formulae (I) and (II):

wherein $R_1$, $R_2$ and $R_4$ are each independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; and X is hydrogen or hydroxyl.

In the second embodiment of the present invention, a method for preparing the norbornene, acrylate and methacrylate monomers by reacting an alcoholic compound containing an oxepan-2-one group, which is represented by Formula (III):

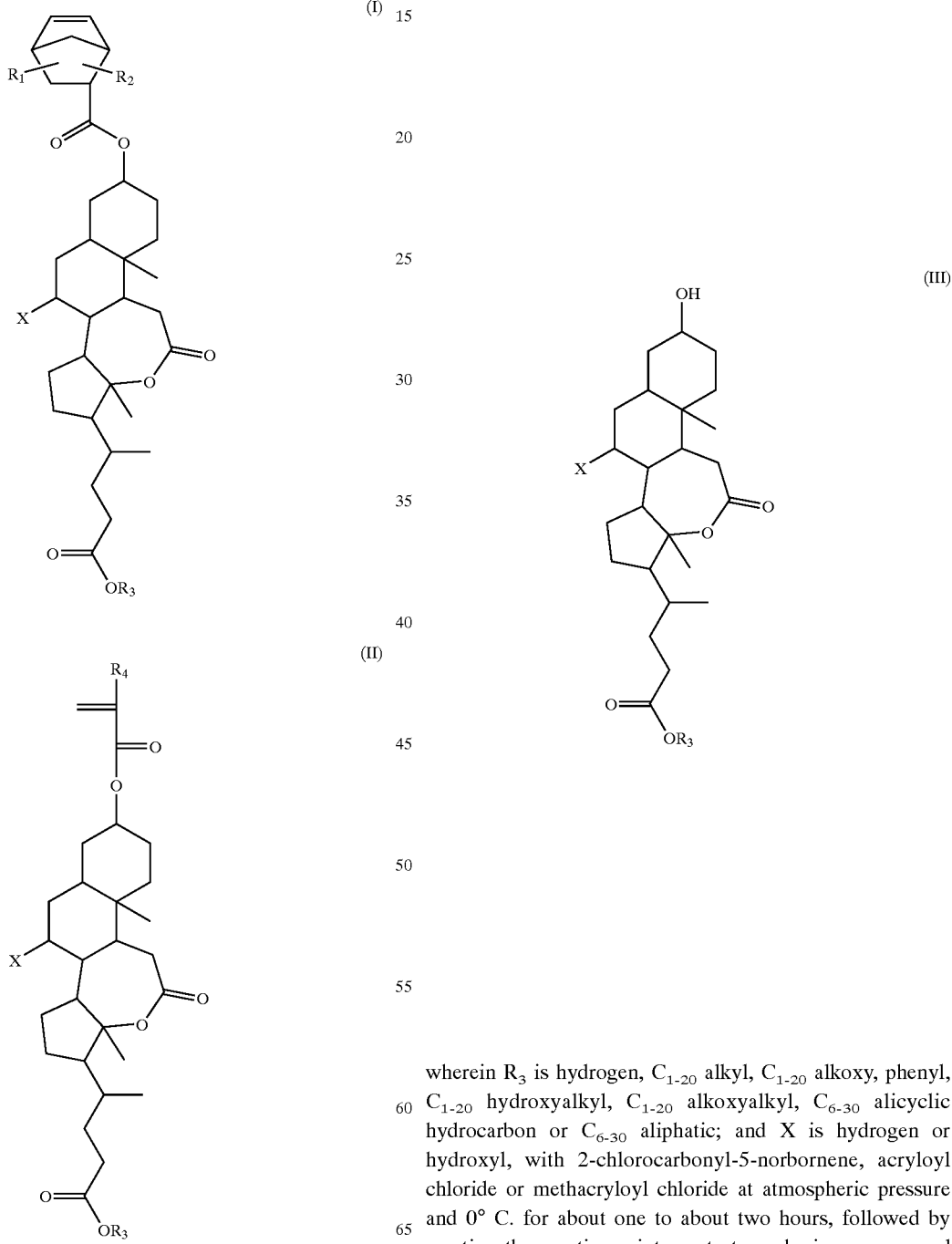

wherein $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic; and X is hydrogen or hydroxyl, with 2-chlorocarbonyl-5-norbornene, acryloyl chloride or methacryloyl chloride at atmospheric pressure and 0° C. for about one to about two hours, followed by reacting the reaction mixture at atmospheric pressure and room temperature for about 5 hours to about 6 hours.

In the third embodiment of the present invention, there is provided a photoresist composition, comprising:

a polymer represented by Formula (IV):

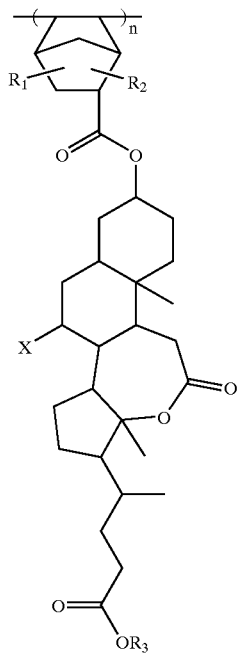

(IV)

wherein $R_1$ and $R_2$ are each independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; X is hydrogen or hydroxyl; and n represents the degree of polymerization and is an integer from about 2 to about 1000, and a photoacid generator.

In accordance with another aspect of the third embodiment of the present invention, there is provided a photoresist composition, comprising:

a polymer represented by Formula (V):

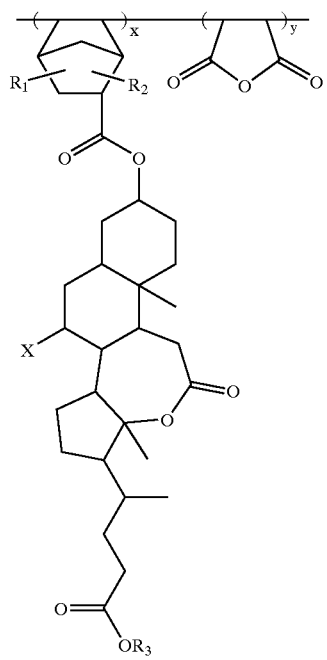

(V)

wherein $R_1$ and $R_2$ are each independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; X is hydrogen or hydroxyl; and x and y each represents molar ratio of each monomer unit and the sum x+y is 1, and a photoacid generator.

In accordance with another aspect of the third embodiment of the present invention, there is provided a photoresist composition, comprising:

a polymer represented by Formula (VI):

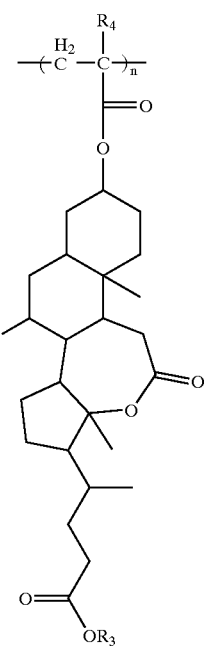

(VI)

wherein $R_1$ and $R_2$ are each independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; X is hydrogen or hydroxyl; and n represents the degree of polymerization and is an integer from about 2 to about 1000, and a photoacid generator.

In the fourth embodiment of the present invention, there is provided a method for preparing a photoresist composition, comprising:

homopolymerizing the norbornene monomer of Formula (I) or copolymerizing the monomer and maleic anhydride to prepare a polymer; and dissolving the polymer and a photoacid generator in a solvent.

Examples of a radical polymerization initiator that can be used for polymerizing the norbornene monomer include, but are not limited to, benzoylperoxide, 2,2-azobisisobutyronitrile, acetylperoxide, laurylperoxide and di-t-butylperoxide.

Examples of solvents used for dissolving the polymer in the present invention include, but are not limited to, benzene, toluene, 1,4-dioxane and tetrahydrofuran. These solvents can be used alone or in combination with two or more solvents. The polymerization is carried out under nitrogen atmosphere at about 50° C. to about 150° C. for about 6 hours to about 30 hours.

The monomer of Formula (I) can be homopolymerized to prepare a polymer which can be used for preparing a photoresist composition. In some embodiments, the monomer of Formula (I) can be copolymerized with a monomer such as maleic anhydride in order to obtain photoresist characteristics, e.g., adhesion to circuit boards and optimal glass transition temperature.

In accordance with another aspect of the fourth embodiment of the present invention, there is provided a method for preparing a photoresist composition, comprising:

homopolymerizing the monomer of Formula (II) or copolymerizing the monomer and maleic anhydride to prepare a polymer; and dissolving the polymer and a photoacid generator in a solvent.

In accordance with another aspect of the fourth embodiment of the present invention, there is provided a method for preparing a photoresist composition, comprising:

homopolymerizing the monomer of Formula (II), or copolymerizing the monomer and an acrylate or methacrylate monomer containing an alicyclic hydrocarbon or aliphatic lactone group, to prepare a polymer; and dissolving the polymer and a photoacid generator in a solvent.

In some embodiments, the content of the photoacid generator used is in the range of about 0.01% to about 20% by weight, based on the weight of the polymer, but is not particularly limited to this range. In some embodiments the solvent is used in an amount of about 10% to about 1,000% by weight, based on the weight of the polymer.

The fifth embodiment of the present invention is directed to a method for forming photoresist patterns, comprising (1) applying the photoresist composition provided from the fourth embodiment on a substrate, to form a photoresist film, (2) exposing the photoresist film to light through a photomask, (3) baking the exposed photoresist film, and (4) developing the baked photoresist film with a conventional developer.

Photoresist developers are known to those in the art. In one embodiment, a developer such as 2.38% (by weight) tetramethylammonium hydroxide aqueous solution can be used.

In conventional photoresist polymers for far ultraviolet, carboxyl protecting groups, e.g., t-butylester groups, acetal groups, and ketal groups, or phenol protecting groups, e.g., t-butoxycarbonyl groups, tetrahydrofuranyl groups, etc., undergo a deprotection reaction to release undesired substances including isobutene, which are volatilized from the photoresist. However, far ultraviolet (248 nm or 193 nm) irradiation on the photoresist film provided in the fifth embodiment and subsequent post-exposure baking enables the formation of carboxylic acid due to a ring-opening reaction, as depicted in Reaction Schemes 1 and 2 below:

Reaction Scheme 1.

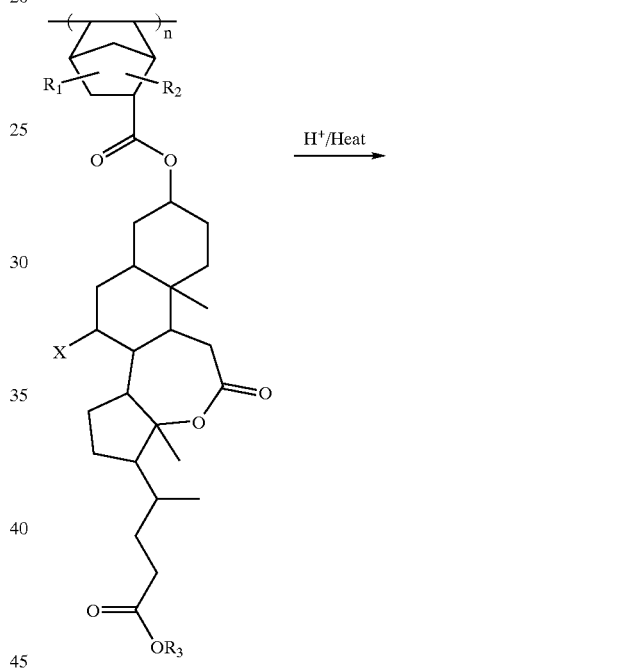

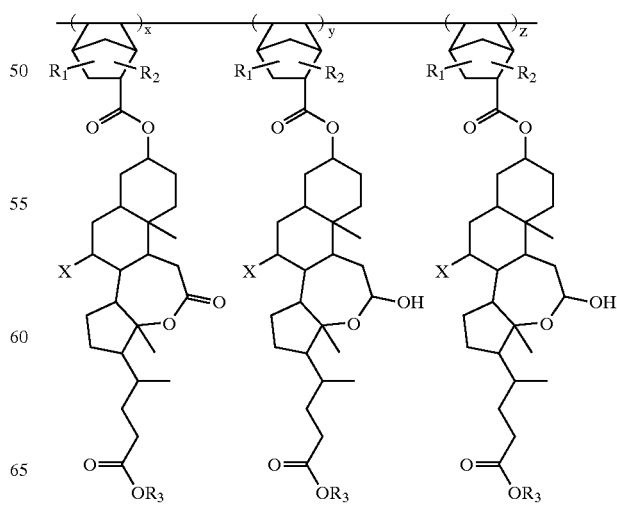

Reaction Scheme 2.

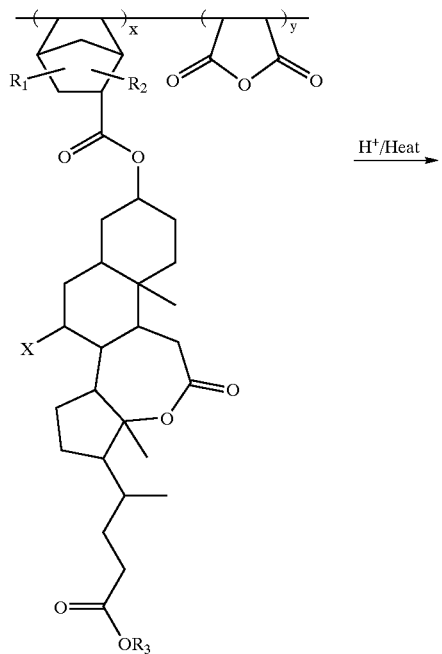

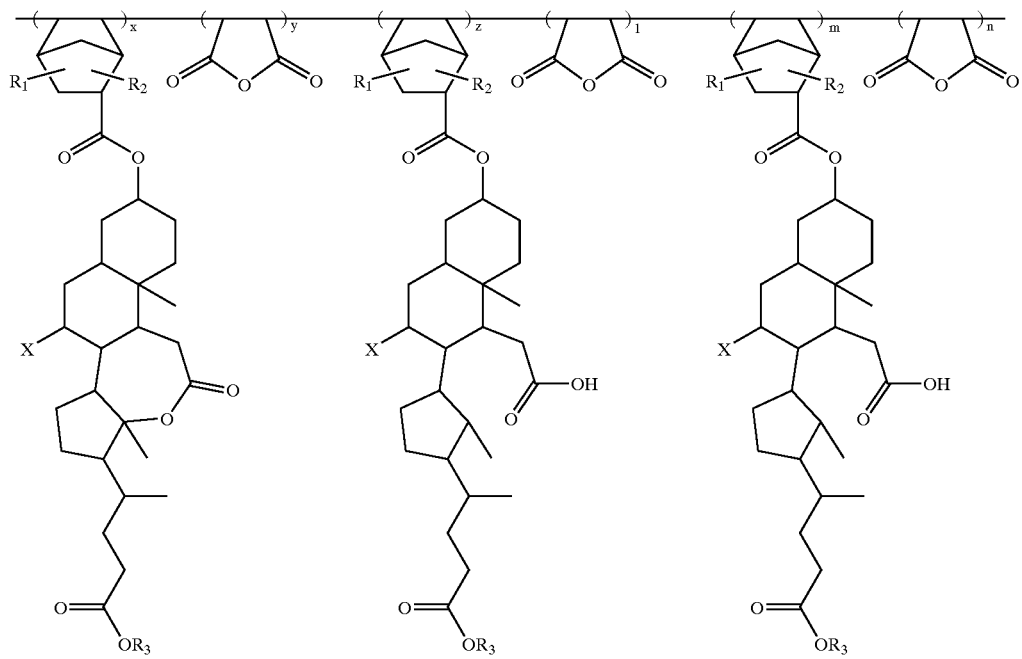

As depicted in Reaction Schemes 1 and 2, since carboxylic acid is formed by a ring-opening reaction instead of deprotection reaction, no low molecular weight substances are volatilized from the photoresist film upon exposure and post-exposure baking. In some embodiments, baking is carried out at about 60° C. to about 140° C. for about 90 seconds to about 120 seconds.

Forming a photoresist film according to the present invention includes (1) dissolving an onium salt such as triphenylsulfonium triflate as a photoacid generator (PAG), and if necessary, another organic photoacid generator, in a solvent such as, but not limited to, propyleneglycol monomethyl-ether acetate, cyclohexanone, ethyllactate and the like, and filtering the solution to obtain a photoresist solution, the photoacid generator being used in an amount of about 0.01% to about 20% by weight, based on the weight of the polymer, (2) spin-coating the solution on a silicon wafer, and (3)

baking the silicon wafer on a hot plate at about 90° C. to about 140° C. for about 90 seconds to about 120 seconds.

The portion of the photoresist film where far ultraviolet is irradiated is subjected to a ring-opening reaction of an oxepan-2-one ring with the catalytic action of an acid generated by exposure and post-exposure baking, forming carboxylic acid as depicted in Reaction Schemes 1 and 2. The unexposed portion is highly stable at post-exposure baking temperatures. Since 2.38% (by weight) of tetramethylammonium hydroxide aqueous solution as a conventional developer dissolves the exposed portion but does not dissolve the unexposed portion, photoresist patterns are formed on the substrate. As a light source for exposure to light, an $F_2$ excimer laser, an Extreme UV source, an e-beam, an X-ray, an ion beam, or a far ultraviolet source can be used without particular limitation.

For preparation of the polymers of the present invention, radical polymerization is carried out by bulk polymerization or solution polymerization. In some embodiments, a solvent used for solution polymerization can be, but is not limited to, cyclohexanone, cyclopentanone, tetrahydrofuran, dimethylformamide, 1,4-dioxane, methylethylketone, benzene, toluene, xylene or mixtures thereof.

In some embodiments, a polymerization initiator can be, but is not limited to, benzoylperoxide, 2,2'-azobisisobutyronitrile, acetylperoxide, laurylperoxide, tert-butylperacetate, tert-butylhydroperoxide or di-tert-butylperoxide.

The present invention provides a photoresist composition comprising at least one polymer prepared as described herein, a photoacid generator and an organic solvent. The photoacid generator is not specifically restricted so long as it can generate an acid upon exposure to light. As the photoacid generator, sulfonate- and onium salt-based compounds can be used. Specific examples of photoacid generators include, but are not limited to, phthalimidotrifluoromethane sulfonate, dinitrobenzyl tosylate, n-decyldisulfone, naphthylimidotrifluoromethane sulfonate, diphenyliodonium hexafluoro phosphate, diphenyliodonium hexafluoro acetate, diphenyliodonium hexafluoro antimonate, diphenylparamethoxyphenyl triflate, diphenylparatoluenyl triflate, triphenylsulfonium triflate, dibutylnaphthylsulfonium triflate and mixtures thereof.

In some embodiments, the photoacid generator is used in an amount of about 0.01% to about 20% by weight, based on the weight of the polymers. When less than about 0.01% by weight of the photoacid generator is used, the photosensitivity of the photoresist is poor. When the photoacid generator is used in an amount exceeding about 20% by weight, it absorbs excessive light, thus resulting in the formation of patterns with a non-uniform cross section.

The organic solvent used for preparing the photoresist composition can be, but is not limited to, diethyleneglycoldiethyl ether, methyl 3-methoxypropionate, ethyl 3-ethoxypropionate, propyleneglycol methylether acetate, cyclohexanone, 2-heptanone, ethyllactate or mixtures thereof. In order to obtain the desired film thickness of the photoresist, in some embodiments the organic solvent can be used in an amount of about 10% to about 1,000% by weight, based on the weight of the photoresist polymer.

As apparent from the description herein, the polymers prepared from the norbornene, acrylate or methacrylate monomer containing an oxepan-2-one group according to the present invention undergo a chemical amplification type ring-opening reaction in the presence of acid, unlike conventional matrix polymers. Accordingly, a large variation of the solubility between the exposed and unexposed portions can be induced.

When the photoresist of the present invention is applied to fine fabrication technology, high sensitivity can be attained and further various problems of conventional photoresists can be solved. For example, contamination of a lens surface in an exposure device system, and problems due to stress generated by a great change in the volume of a photoresist film, e.g., low productivity and pattern deformation, can be solved.

In addition, the photoresist compositions of the present invention comprising the photoresist polymers exhibit a high light transmittance in the far UV region, particularly, 193 nm, excellent etch resistance and thermal stability.

Furthermore, the photoresist compositions are ring-opened upon exposure to light and baking to generate carboxylic acid, which causes a large variation in the polarity. Accordingly, conventional developers can be used to develop the baked photoresist.

In conclusion, the present invention provides not only modified and improved structures of conventional photoresist polymers, but also a new concept of photoresists which solves problems of conventional photoresists.

I. Preparation of Photoresist Monomers

EXAMPLE 1

Preparation of Methyl Deoxycholate 100 g of deoxycholic acid was dissolved in 300 ml of methanol, and then 2 ml of hydrochloric acid was added thereto. The resulting mixture was refluxed for 1 hour. The methanol was distilled off. After the resulting mixture was dissolved in 400 ml of ethylether, it was washed with distilled water, sodium bicarbonate and brine several times. The separated organic layer was dried over anhydrous magnesium sulfate, concentrated and dried in vacuo to prepare 95 g (yield: 92%) of methyl deoxycholate represented by the following formula:

$^1$H-NMR (CDCl$_3$, ppm): δ=3.94 (s, 1H, H$^{12}$), 3.63 (s, 3H, COOMe), 3.50–3.59 (m, 1H, H$^3$), 2.10–2.49 (m, 2H, CH$_2$, H$^{23}$), 1.10–1.90 (m, 26H), 0.93 (d, 3H, CH$_3$, H$^{21}$), 0.87 (s, 3H, CH$_3$, H$^{19}$), 0.64 (s, 3H, CH$_3$, H$^{18}$)

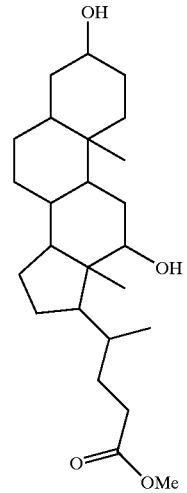

EXAMPLE 2

Preparation of Methyl Deoxycholate 3α-acetate 63 g of methyl deoxycholate and pyridine (75 ml) were sufficiently dissolved in 300 ml of benzene, and then 74 ml of acetic acid anhydride was slowly added thereto. The mixture was stirred for 24 hours. After the mixture was cooled on ice at 0° C., it was further stirred for 30 minutes. The benzene layer was separated and washed with water several times. The benzene solution was concentrated, and dried in vacuo to prepare 62 g (yield: 90%) of methyl deoxycholate 3α-acetate represented by the following formula:

$^1$H-NMR (CDCl$_3$, ppm): δ=4.62–4.70 (m, 1H, H$^3$) 3.63 (s, 3H, COOMe), 2.10–2.49 (m, 2H, CH$_2$, H$^{23}$), 2.00 (s, 3H, OCOCH$_3$) 1.90–2.00 (m, 2H, H$^{11}$), 1.10–1.90 (m, 26H), 0.93(d, 3H, CH$_3$, H$^{21}$), 0.87 (s, 3H, CH$_3$, H$^{19}$), 0.64 (s, 3H, CH$_3$, H$^{18}$)

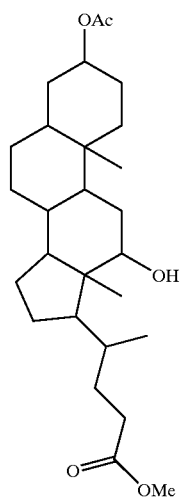

EXAMPLE 3

Preparation of Methyl 3α-acetoxy-12-ketodeoxycholanate 25 g of methyl deoxycholate 3α-acetate was sufficiently dissolved in 400 mL of acetic acid, and then aqueous potassium chromate (16 g) solution was slowly added thereto. The resulting solution was stirred at room temperature for 12 hours. After the solution was added to 1.5L of distilled water, it was stirred for 1 hour and filtered. The obtained precipitate was washed with distilled water several times, and dried to obtain a white solid. The obtained solid was recrystallized from methanol to prepare 23.5 g (yield: 95%) of pure methyl 3α-acetoxy-12-ketocholanate represented by the following formula:

$^1$H-NMR (CDCl$_3$, ppm): δ=4.62–4.70 (m, 1H, H$^3$), 3.63 (s, 3H, COOMe), 2.10–2.49 (m, 2H, CH$_2$, H$^{23}$), 2.00 (s, 3H, OCOCH$_3$) 1.90–2.00 (m, 2H, H$^{11}$), 1.10–1.90 (m, 26H), 0.93 (d, 3H, CH$_3$, H$^{21}$), 0.87 (s, 3H, CH$_3$, H$^{19}$), 0.64 (s, 3H, CH$_3$, H$^{19}$)

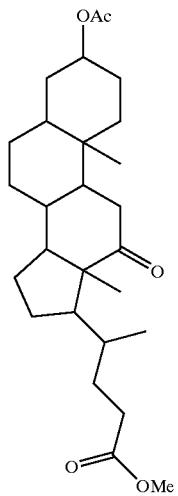

EXAMPLE 4

Preparation of Methyl 3α-hydroxy-12-ketodeoxycholanate 31 g of methyl 3α-acetoxy-12-ketodeoxycholanate was dissolved in 10% aqueous sodium methoxide-methanol solution. The reaction solution was stirred for 24 hours. After the reaction solution was cooled to 0° C., it was neutralized by addition of hydrochloric acid. The obtained mixture was concentrated and then dissolved in 200 ml of ether. The resulting solution was washed with distilled water and brine several times, dried over magnesium sulfate, concentrated, and dried in vacuo to prepare 27 g (yield: 97%) of methyl 3-hydroxy-12-ketodeoxycholanate represented by the following formula:

$^1$H-NMR (CDCl$_3$, ppm): δ=3.59 (s, 3H, COOMe, H$^{18}$), 3.50–3.59 (m, 1H, H$^3$), 2.10–2.49 (m, 2H, CH$_2$, H$^{23}$), 1.90–2.00 (m, 2H, H$^{11}$), 1.10–1.90 (m, 26H), 0.93 (d, 3H, CH$_3$, H$^{21}$), 0.87 (s, 3H, CH$_3$, H$^{19}$), 0.64 (s, 3H, CH$_3$, H$^{18}$)

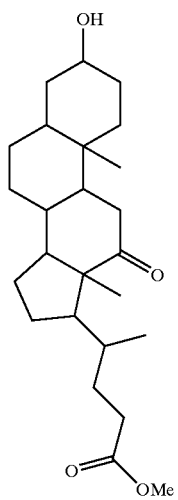

EXAMPLE 5

Preparation of Methyl 4-(7-hydroxy-9α,12α-dimethyl-11-oxo-hexadecahydro-12-oxa-naphtho[2,1-e]azulen-1-yl)-pentanoate 41.56 g of 3-chloroperoxybezonic acid (mCPBA, purity: 77%) and 10.38 g of sodium bicarbonate were added to methylene chloride, and then a solution of 25 g of methyl 3-hydroxy-12-ketocholanate in methylene chloride was slowly added thereto. After the reaction solution was stirred at room temperature for 24 hours, aqueous sodium sulfite solution was added thereto. The resulting solution was stirred for 30 minutes. The solution was diluted with methylene chloride, and was washed with aqueous potassium carbonate solution and brine several times. The diluted solution was dried over magnesium sulfate, concentrated, and purified by column chromatography (eluent: ethylacetate/hexane (1/3)) to prepare 10.37 g (yield: 41%) of methyl 4-(7-hydroxy-9α,12α-dimethyl-11-oxo-hexadecahydro-12-oxa-naphtho[2,1-e]azulen-1-yl)-pentanoate represented by the following formula:

$^1$H-NMR (CDCl$_3$, ppm): δ=3.59 (s, 3H, COOMe, H$^{18}$), 3.50–3.59 (m, 1H, H$^3$), 2.45–2.60 (d, 2H, COOMe of lactone); FT-IR (cm$^{-1}$): 3464 (OH), 1732 (ester of ketone), 1171 (ether bond of ester)

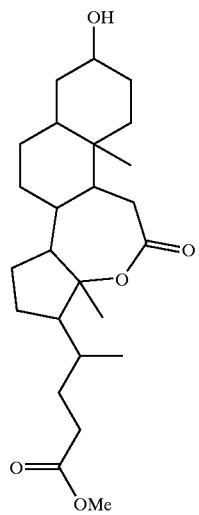

EXAMPLE 6

Preparation of bicyclo[2.2.1]hepta-5-ene-2-carboxylic acid 1-(3-methoxycarbonyl-1-methylpropyl)-9α,12α-dimethyl-11-oxo-hexadecahydro-12-oxa-naphtho[2,1-e]azulen-7-yl ester 10 g of methyl 4-(7-hydroxy-9α,12α-dimethyl-11-oxo-hexadecahydro-12-oxa-naphtho[2,1-e]azulen-1-yl)-pentanoate was sufficiently dissolved in 200 ml of dry tetrahydrofuran under nitrogen atmosphere, and then triethylamine (5.12 ml) was added thereto. After the solution was cooled to 0° C., a solution of 4.6 g of 2-chlorocarbonyl-5-norbornene in 50 ml of tetrahydrofuran was slowly added thereto. The reaction solution was stirred for 6 hours. After the reaction solution was added to 25 ml of ice water at 0° C., it was stirred for 30 minutes and then 500 ml of ether was added thereto. The organic layer was separated, and washed with aqueous sodium bicarbonate solution several times and subsequently with distilled water twice. The resulting organic solution was concentrated, and purified by column chromatography (eluent: ethylacetate/hexane (1/3)) to prepare 10.9 g (yield: 83%) of pure bicyclo[2.2.1]hepta-5-ene-2-carboxylic acid 1-(3-methoxycarbonyl-1-methylpropyl)-9α,12α-dimethyl-11-oxo-hexadecahydro-12-oxa-naphtho[2,1-e]azulen-7-yl ester represented by the following formula:

$^1$H-NMR (CDCl$_3$, ppm): δ=5.86–6.16 (m, 2H, olefin proton), 2.45–2.60 (d, 2H, COOMe of lactone); FT-IR (cm$^{-1}$): 1732 (ketone of ester), 1130 (ether bond of ester)

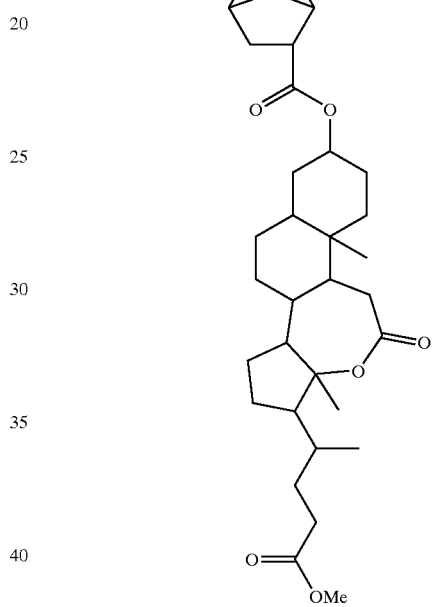

EXAMPLE 7

Preparation of 2-methacrylic acid 1-(3-methoxycarbonyl-1-methylpropyl)-9α,12α-dimethyl-11-oxo-hexadecahydro-12-oxa-naphtho[2,1-e]azulen-7-yl ester 9.5 g (yield: 85%) of 2-methacrylic acid 1-(3-methoxycarbonyl-1-methylpropyl)-9α,12α-dimethyl-11-oxo-hexadecahydro-12-oxa-naphtho[2,1-e]azulen-7-yl ester was prepared in the same manner as in Example 6, except that 4 g of methacryloyl chloride was used. The title compound thus prepared is represented by the following formula:

H-NMR (CDCl$_3$, ppm): δ=5.90–6.16 (m, 2H, olefin proton), 2.45–2.60 (d, 2H, COOMe of lactone); FT-IR (cm$^-$1): 1732 (ketone of ester), 1130 (ether bond of ester)

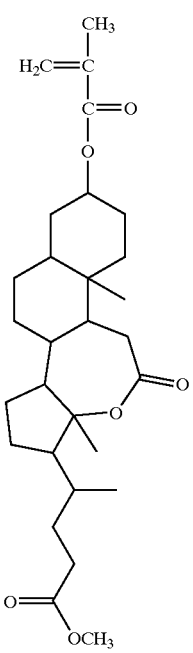

EXAMPLE 8

Preparation of Methyl Cholate 95 g (95%) of methyl cholate was prepared in the same manner as in Example 1, except that 100 g of cholic acid was used instead of deoxycholic acid. The title compound thus prepared is represented by the following formula:

$^1$H-NMR (CDCl$_3$, ppm): δ=3.94 (s, 1H, H$^{12}$), 3.87 (m, 1H, H$^7$), 3.63 (s, 3H, COOMe), 3.50–3.59 (m, 1H, H$^3$), 2.10–2.49 (m, 2H, CH$_2$, H$^{23}$), 1.10–1.90 (m, 26H), 0.93 (d, 3H, CH$_3$, H$^{21}$), 0.87 (s, 3H, CH$_3$, H$^{19}$), 0.64 (s, 3H, CH$_3$, H$^{18}$)

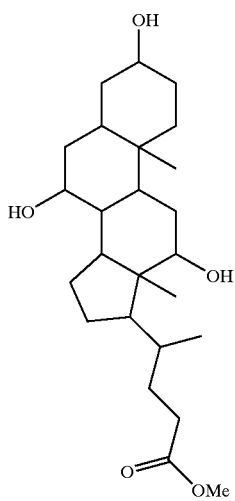

EXAMPLE 9

Preparation of Methyl Cholate 3α,7α-diacetate 65 g (yield: 92%) of methyl cholate 3α,7α-diacetate was prepared in the same manner as in Example 2, except that 65 g of methyl cholate was used instead of methyl deoxycholate. The title compound thus prepared is represented by the following formula:

$^1$H-NMR (CDCl$_3$, ppm): δ=4.62–4.70 (m, 1H, H$^3$), 3.63 (s, 6H, COOMe), 2.10–2.49 (m, 2H, CH$_2$, H$^{23}$), 2.00 (s, 3H, OCOCH$_3$) 1.90–2.00 (m, 2H, H$^{11}$), 1.10–1.90 (m, 26H), 0.93 (d, 3H, CH$_3$, H$^{21}$), 0.87 (s, 3H, CH$_3$, H$^{19}$), 0.64 (s, 3H, CH$_3$, H$^{18}$)

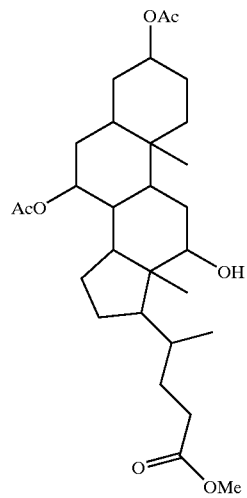

EXAMPLE 10

Preparation of Methyl 3α,7α-diacetoxy-12-ketocholanate 24 g (yield: 95%) of methyl 3α,7α-diacetoxy-12-ketocholanate was prepared in the same manner as in Example 3, except that 28 g of methyl 3α,7α-diacetate was used instead of methyl 3α-acetate. The title compound thus prepared is represented by the following formula:

$^1$H-NMR (CDCl$_3$, ppm): δ=3.59 (s, 3H, COOMe, H$^{18}$), 3.50–3.59 (m, 1H, H$^3$), 2.10–2.49 (m, 2H, CH$_2$, H$^{23}$), 1.90–2.00 (m, 2H, H$^{11}$), 1.10–1.90 (m, 26H), 0.93 (d, 3H, CH$_3$, H$^{21}$), 0.87 (s, 3H, CH$_3$, H$^{19}$), 0.64 (s, 3H, CH$_3$, H$^{18}$)

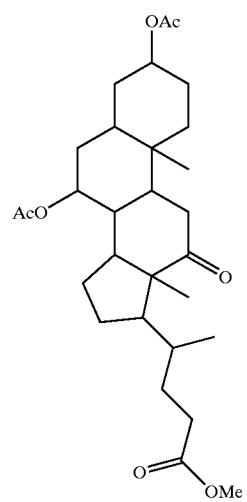

EXAMPLE 11

Preparation of Methyl 3α,7α-dihydroxy-12-ketocholanate 29 g (yield: 96%) of methyl 3α,7α-dihydroxy-12-ketocholanate was prepared in the same manner as in Example 4, except that 32 g of methyl 3α,7α-diacetoxy-12-ketocholanate was used instead of methyl 3α-acetoxy-12-ketocholanate. The title compound thus prepared is represented by the following formula:

$^1$H-NMR (CDCl$_3$, ppm): δ=3.87 (m, 1H, H$^7$), 3.59 (s, 3H, COOMe, H$^{18}$), 3.50–3.59 (m, 1H, H$^3$), 2.10–2.49 (m, 2H, CH$_2$, H$^{23}$), 1.90–2.00 (m, 2H, H$^{11}$), 1.10–1.90 (m, 26H), 0.93 (d, 3H, CH$_3$, H$^{21}$), 0.87 (s, 3H, CH$_3$, H$^{19}$), 0.64 (s, 3H, CH$_3$, H$^{18}$)

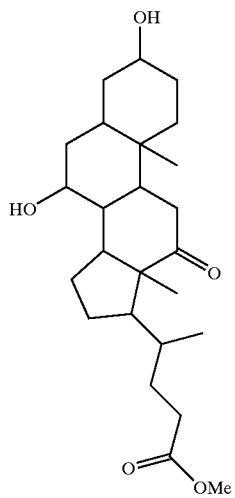

EXAMPLE 12

Preparation of Methyl 4-(4,7-dihydroxy-9α,12α-dimethyl-11-oxo-hexadecahydro-12-oxa-naphtho[2,1-e]azulen-1-yl)-pentanoate 11 g (yield: 42%) of methyl 4-(4,7-dihydroxy-9α,12α-dimethyl-11-oxo-hexadecahydro-12-oxa-naphtho[2,1-e]azulen-1-yl)-pentanoate was prepared in the same manner as in Example 5, except that 28 g of methyl 3α,7α-dihydroxy-12-ketocholanate was used instead of methyl 3α-hydroxy-12-ketocholanate. The title compound thus prepared is represented by the following formula:

$^1$H-NMR (CDCl$_3$, ppm): δ=3.87 (m, 1H, H$^7$), 3.59 (s, 3H, COOMe, H$^{18}$), 3.50–3.59 (m, 1H, H$^3$), 2.45–2.60 (d, 2H, CH$_2$COO of lactone); FT-IR (cm$^{-1}$): 3464 (OH), 1732 (ester of ketone), 1171 (ether bond of ester)

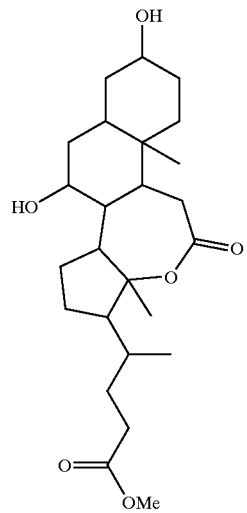

EXAMPLE 13

Preparation of bicyclo[2.2.1]hepta-5-ene-2-carboxylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester 12 g (yield: 85%) of bicyclo[2.2.1]hepta-5-ene-2-carboxylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester was prepared in the same manner as in Example 6, except that 11 g of methyl 4-(4,7-dihydroxy-9α,12α-dimethyl-11-oxo-hexadecahydro-12-oxa-naphtho[2,1-e]azulen-1-yl)-pentanoate was used instead of methyl 4-(7-hydroxy-9α,12α-dimethyl-11-oxo-hexadecahydro-12-oxa-naphtho[2,1-e]azulen-1-yl)-pentanoate. The title compound thus prepared is represented by the following formula:

$^1$H-NMR (CDCl$_3$, ppm): δ=5.90–6.16 (m, 2H, olefin proton), 2.45–2.60 (d, 2H, CH$_2$COO of lactone); FT-IR (cm$^{-1}$): 3464 (OH), 1732 (ester of ketone), 1171 (ether bond of ester)

(I)

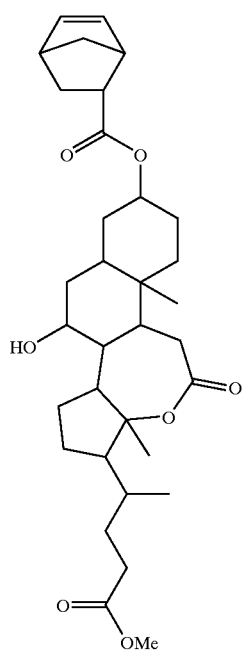

EXAMPLE 14

Preparation of 2-methacrylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester 9.8 g (yield: 84%) of 2-methacrylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester was prepared in the same manner as in Example 13, except that 4.2 g of methacryloyl chloride was used. The title compound thus prepared is represented by the following formula:

$^1$H-NMR (CDCl$_3$, ppm): δ=5.90–6.16 (m, 2H, olefin proton), 2.45–2.60 (d, 2H, CH$_2$COO of lactone); FT-IR (cm$^{-1}$): 3464 (OH), 1732 (ester of ketone), 1171 (ether bond of ester)

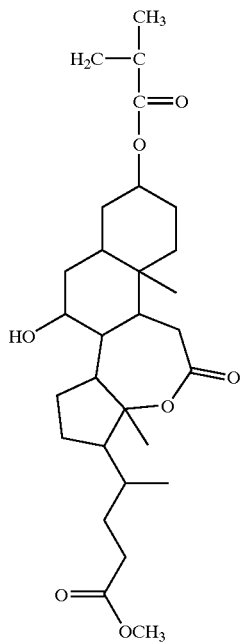

II. Preparation of Photoresist Polymers

EXAMPLE 15

Preparation of bicyclo[2.2.1]hepta-5-ene-2-carboxylic acid 1-(3-methoxycarbonyl-1-methylpropyl)-9α, 12α-dimethyl-11-oxo-hexadecahydro-12-oxa-naphtho[2,1-e]azulen-7-yl ester polymer 5 g of bicyclo[2.2.11]hepta-5-ene-2-carboxylic acid 1-(3-methoxycarbonyl-1-methylpropyl)-9α,12α-dimethyl-11-oxo-hexadecahydro-12-oxa-naphtho[2,1-e]azulen-7-yl ester, 0.9 g of maleic anhydride, and 0.03 g of 2,2'-azobisisobutyronitrile as a radical polymerization initiator were charged into a polymerization flask, and were sufficiently dissolved in 6.0 g of purified tetrahydrofuran. The solution was polymerized under nitrogen atmosphere at 65° C. for 24 hours. After the polymerization was completed, the reaction solution was precipitated in a mixed solvent of petroleum ether and ethylether (3:1) and filtered. The obtained precipitate was dried in vacuo to prepare 1.8 g (yield: 30%) of poly((bicyclo[2.2.1]hepta-5-ene-2-carboxylic acid 1-(3-methoxycarbonyl-1-methylpropyl)-9α,12α-dimethyl-11-oxo-hexadecahydro-12-oxa-naphtho[2,1-e]azulen-7-yl ester)-co-maleic anhydride).

EXAMPLE 16

Preparation of 2-methacrylic acid 1-(3-methoxycarbonyl-1-methylpropyl)-9α,12α-dimethyl-11-oxo-hexadecahydro-12-oxa-naphtho[2,1-e]azulen-7-yl ester polymer 2.6 g (yield: 65%) of poly((2-methacrylic acid 1-(3-methoxycarbonyl-1-methylpropyl)-9α,12α-dimethyl-11-oxo-hexadecahydro-12-oxa-naphtho[2,1-e]azulen-7-yl ester) was prepared in the same manner as in Example 15, except that 4.4 g of 2-methacrylic acid 1-(3-methoxycarbonyl-1-methylpropyl)-9α,12α-dimethyl-11-oxo-hexadecahydro-12-oxa-naphtho[2,1-e]azulen-7-yl ester and 0.03 g of 2,2-azobisisobutyronitrile were used.

EXAMPLE 17

Preparation of bicyclo[2.2.1]hepta-5-ene-2-carboxylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester polymer 1.85 g (yield: 30%) of poly((bicyclo[2.2.1]hepta-5-ene-2-carboxylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester)-co-maleic anhydride) was prepared in the same manner as in Example 15, except that 5.2 g of bicyclo[2.2.1]hepta-5-ene-2-carboxylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester was used.

EXAMPLE 18

Preparation of 2-methacrylic acid 4-hydroxy-1-(3-methoxycarbonyl-1-methylpropyl)-9α,12α-dimethyl-11-oxo-hexadecahydro-12-oxa-naphtho [2,1-e]azulen-7-yl ester polymer 3.4 g (yield: 62%) of poly(2-methacrylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester) was prepared in the same manner as in Example 16, except that 5 g of 2-methacrylic acid 4-hydroxy-1-(3-methoxycarbonyl-1-methylpropyl)-9α,12α-dimethyl-11-oxo-hexadecahydro-12-oxa-naphtho[2,1-e]azulen-7-yl ester and 0.03 g of 2,2-azobisisobutyronitrile were used.

III. Preparation of Photoresist Compositions and Patterning Method Using the Compositions

EXAMPLE 19

Preparation of Photoresist Composition and Patterning Method Using the Composition 0.2 g of the polymer prepared in Example 15 and 0.004 g of triphenylsulfonium triflate as a photoacid generator were dissolved in 1.5 g of propyleneglycol monomethylether acetate in a laboratory in which far ultraviolet radiation was completely blocked, and passed through a filter having a mesh size of 0.2 μm to prepare a photoresist composition. The photoresist composition thus prepared was spin-coated on a silicon wafer, and baked at 100° C. for 90 seconds to fabricate a photoresist film having a thickness of 0.4 μm. After baking, the photoresist film was exposed to light using an ArF excimer laser exposure device, and then baked at 120° C. for 90 seconds. Thereafter, the baked film was developed with 2.38% (by weight) tetramethylammonium hydroxide aqueous solution for 90 seconds to form patterns of 0.3 μm (see FIG. 1).

EXAMPLE 20

Preparation of Photoresist Composition and Patterning Method Using the Composition Patterns of 0.31 μm were formed in the same manner as in Example 19, except that the polymer prepared in Example 16 was used.

EXAMPLE 21

Preparation of Photoresist Composition and Patterning Method Using the Composition Patterns of 0.3 μm were formed in the same manner as in Example 19, except that the polymer prepared in Example 17 was used.

EXAMPLE 22

Preparation of Photoresist Composition and Patterning Method Using the Composition Patterns of 0.31 μm were formed in the same manner as in Example 19, except that the polymer prepared in Example 18 was used.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A norbornene monomer represented by Formula (I):

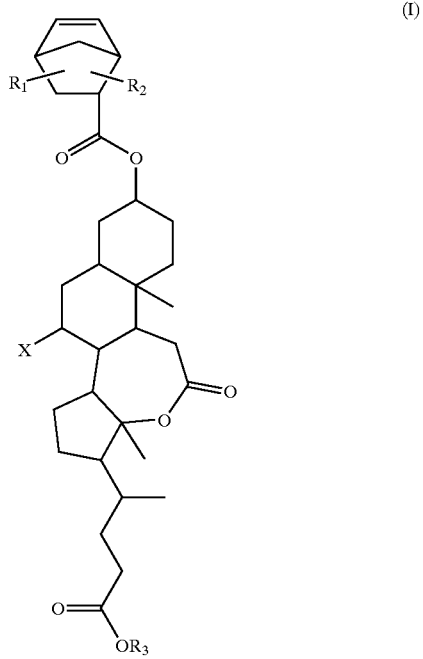

(I)

wherein $R_1$ and $R_2$ are each independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; and X is hydrogen or hydroxyl.

2. A method of preparing the monomer of Formula (I) as defined in claim 1 by reacting the alcoholic compound represented by Formula (III):

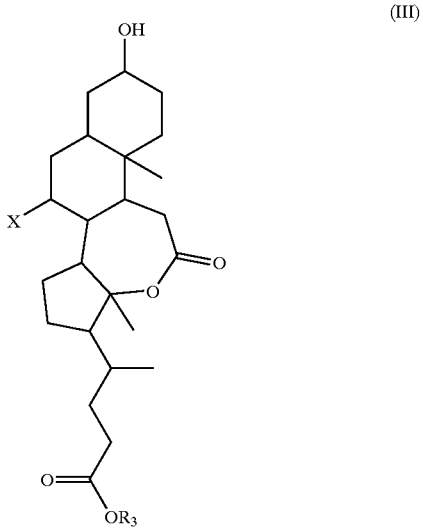

(III)

wherein $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; and X is hydrogen or hydroxyl, with 2-chlorocarbonyl-5-norbornene.

3. A method of preparing a photoresist composition, comprising:

homopolymerizing the norbornene monomer of Formula (I) as defined in claim 1, or copolymerizing the monomer of Formula (I) and maleic anhydride, to prepare a polymer; and dissolving the polymer and a photoacid generator in a solvent.

4. The method of claim 3, wherein the solvent is used in an amount of about 10% to about 1000% by weight, based on the weight of the polymer.

5. An acrylate or methacrylate monomer represented by Formula (II):

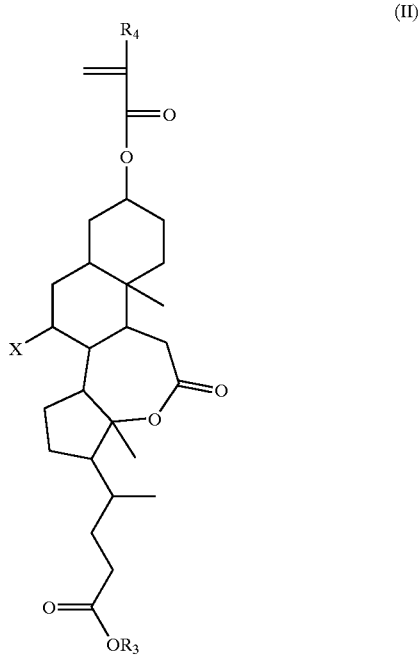

(II)

wherein $R_4$ is independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; and X is hydrogen or hydroxyl.

6. A method of preparing the monomer of Formula (II) as defined in claim 5 by reacting the alcoholic compound represented by Formula (III):

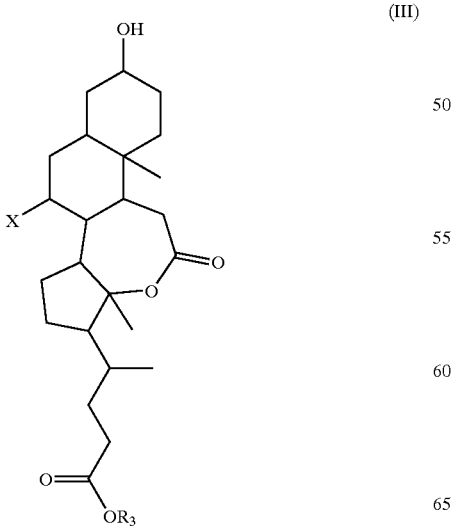

(III)

wherein $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; and X is hydrogen or hydroxyl, with a compound selected from acryloyl chloride and methacryloyl chloride.

7. A method of preparing a photoresist composition, comprising:

homopolymerizing the monomer of Formula (II) as defined in claim 5, or copolymerizing the monomer of Formula (II) and maleic anhydride, to prepare a polymer; and dissolving the polymer and a photoacid generator in a solvent.

8. The method of claim 7, wherein the solvent is used in an amount of about 10% to about 1000% by weight, based on the weight of the polymer.

9. A method of preparing a photoresist composition, comprising:

mixing the monomer of Formula (II) as defined in claim 5, and an acrylate or methacrylate monomer containing an alicyclic hydrocarbon or aliphatic lactone group, to prepare a polymer; and dissolving the polymer and a photoacid generator in a solvent.

10. The method of claim 9, wherein the solvent is used in an amount of about 10% to about 1000% by weight, based on the weight of the polymer.

11. An alcoholic compound represented by Formula (III):

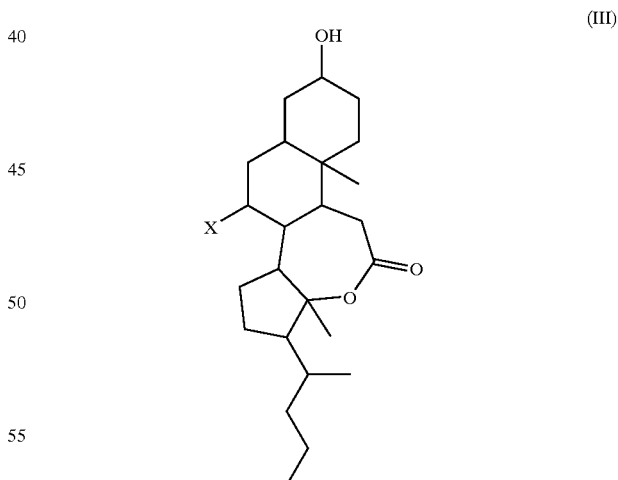

(III)

wherein $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; and X is hydrogen or hydroxyl.

12. A polymer represented by Formula (IV):

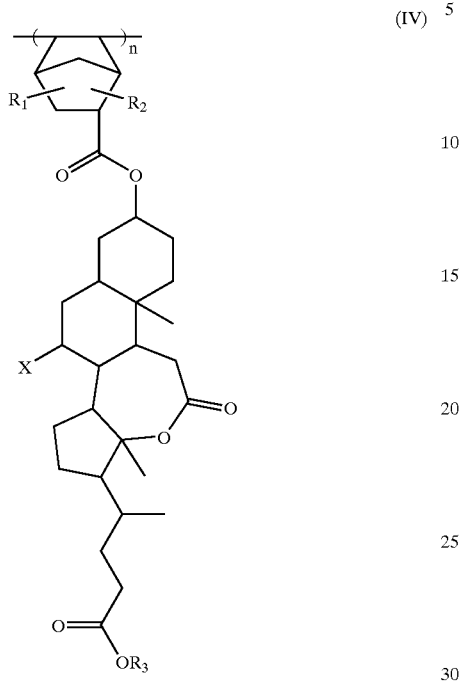

wherein $R_1$ and $R_2$ are each independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; X is hydrogen or a hydroxyl; and n represents the degree of polymerization and is an integer from 2 to 1000.

13. A photoresist composition comprising the polymer of Formula (IV) in claim 12, and a photoacid generator.

14. The photoresist composition of claim 13, wherein the photoacid generator is added in an amount of about 0.01% to about 20% by weight, based on the weight of the polymer.

15. A method of forming photoresist patterns, comprising:

(a) applying the photoresist composition of claim 13 on a substrate, to form a photoresist film;

(b) exposing the photoresist film to light;

(c) baking the exposed photoresist film; and (d) developing the baked photoresist film to form desired patterns.

16. The method of claim 15, wherein the baking in (c) is carried out at about 60° C. to about 140° C.

17. The method of claim 15, wherein the exposing in (b) is carried out by using a far ultraviolet, an $F_2$ excimer laser, an extreme UV, an e-beam, an X-ray or an ion beam light source.

18. A polymer represented by Formula (V):

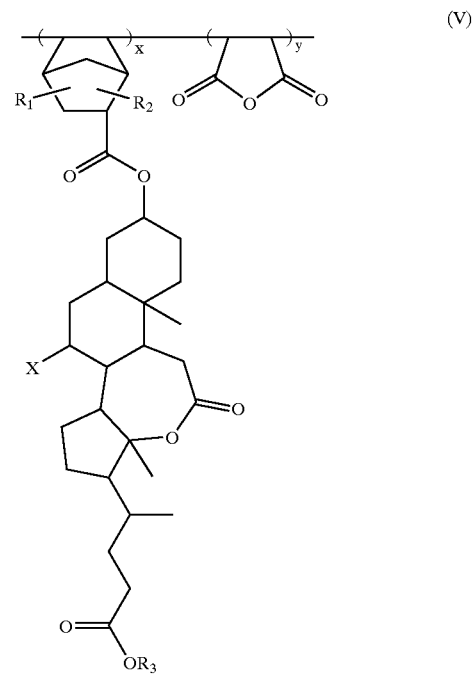

wherein $R_1$ and $R_2$ are each independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; X is hydrogen or hydroxyl; and x and y each represents a molar ratio of each monomer unit and the sum x+y is 1.

19. A photoresist composition comprising the polymer of Formula (V) as defined in claim 18, and a photoacid generator.

20. The photoresist composition of claim 19, wherein the photoacid generator is added in an amount of about 0.01% to about 20% by weight, based on the weight of the polymer.

21. A method of forming photoresist patterns, comprising:

(a) applying the photoresist composition of claim 19 on a substrate, to form a photoresist film;

(b) exposing the photoresist film to light;

(c) baking the exposed photoresist film; and (d) developing the baked photoresist film to form desired patterns.

22. The method of claim 21, wherein the baking in (c) is carried out at about 60° C. to about 140° C.

23. The method of claim 21, wherein the exposing in (b) is carried out by using a far ultraviolet, an $F_2$ excimer laser, an extreme UV, an e-beam, an X-ray or an ion beam light source.

24. A polymer represented by Formula (VI):

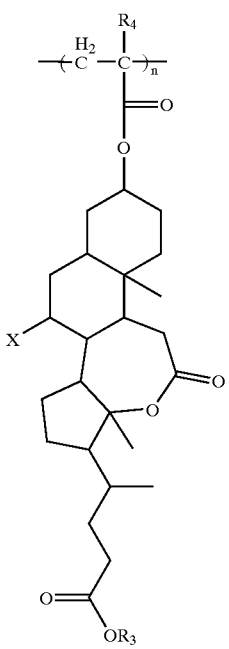

(VI)

wherein $R_4$ is each independently hydrogen, $C_{1-4}$ alkyl, $C_{1-4}$ alkoxy or phenyl; $R_3$ is hydrogen, $C_{1-20}$ alkyl, $C_{1-20}$ alkoxy, phenyl, $C_{1-20}$ hydroxyalkyl, $C_{1-20}$ alkoxyalkyl, $C_{6-30}$ alicyclic hydrocarbon or $C_{6-30}$ aliphatic lactone; X is hydrogen or hydroxyl; and n represents the degree of polymerization and is an integer from 2 to 1000.

25. A photoresist composition comprising the polymer of Formula (VI) as defined in claim 24, and a photoacid generator.

26. The photoresist composition of claim 25, wherein the photoacid generator is added in an amount of about 0.01% to about 20% by weight, based on the weight of the polymer.

27. A method of forming photoresist patterns, comprising:

(a) applying the photoresist composition of claim 25 on a substrate, to form a photoresist film;

(b) exposing the photoresist film to light;

(c) baking the exposed photoresist film; and (d) developing the baked photoresist film to form desired patterns.

28. The method of claim 27, wherein the baking in (c) is carried out at about 60° C. to about 140° C.

29. The method of claim 27, wherein the exposing in (b) is carried out by using a far ultraviolet, an $F_2$ excimer laser, an extreme UV, an e-beam, an X-ray or an ion beam light source.

* * * * *